United States Patent
King et al.

(10) Patent No.: US 12,209,021 B2
(45) Date of Patent: Jan. 28, 2025

(54) ZINC OXIDE GRAPHENE COMPOSITE

(71) Applicant: WiSys Technology Foundation, Inc., Madison, WI (US)

(72) Inventors: Seth Thomas King, Holmen, WI (US); Daniel John Little, Onalaska, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 673 days.

(21) Appl. No.: 17/594,087

(22) PCT Filed: Apr. 1, 2020

(86) PCT No.: PCT/US2020/026254
§ 371 (c)(1),
(2) Date: Oct. 1, 2021

(87) PCT Pub. No.: WO2020/206027
PCT Pub. Date: Oct. 8, 2020

(65) Prior Publication Data
US 2022/0185675 A1    Jun. 16, 2022

Related U.S. Application Data

(60) Provisional application No. 62/828,001, filed on Apr. 2, 2019.

(51) Int. Cl.
*C01B 32/194* (2017.01)

(52) U.S. Cl.
CPC ........ *C01B 32/194* (2017.08); *C01B 2204/22* (2013.01); *C01P 2002/60* (2013.01); *C01P 2002/72* (2013.01); *C01P 2002/82* (2013.01); *C01P 2002/85* (2013.01); *C01P 2004/03* (2013.01); *C01P 2004/50* (2013.01)

(58) Field of Classification Search
CPC ........ B01J 37/08; B01J 37/086; B01J 37/088; B01J 35/33; B01J 35/39; B01J 21/18; B01J 23/06; C01B 32/194; C01B 2204/22; C01B 32/182; C01B 32/198; C01P 2002/60; C01P 2002/72; C01P 2008/82; C01P 2002/85; C01P 2004/03; C01P 2004/50
USPC ................................................. 502/183, 343
See application file for complete search history.

(56) References Cited

U.S. PATENT DOCUMENTS 8,611,070 B2    12/2013  Ivanovici et al.
11,059,031 B2 *  7/2021  Yang ................... B01J 37/088

FOREIGN PATENT DOCUMENTS

| CN | 104465118 A | * | 3/2015 | ........... C01B 32/182 |
| KR | 20150131833 A | * | 11/2015 | ............... B82B 3/00 |
| KR | 20190097410 A | * | 8/2019 | ............. C09K 11/54 |
| WO | WO-2018188772 A1 | | 10/2018 | |
| WO | WO-2020206027 A1 | | 10/2020 | |

OTHER PUBLICATIONS

Thangavelu Kavitha et al., "Glucose sensing, photocatalytic and antibacterial properties of graphene-ZnO nanoparticle hybrids." Carbon, 50, pp. 2994-3000. (Year: 2012).*
Bo Weng et al., "Toward the enhanced photoactivity and photostability of ZnO nanospheres via intimate surface coating with reduced graphene oxide." Journal of Materials Chemistry A, 2, pp. 9380-9389. (Year: 2014).*
"International Application Serial No. PCT US2020 026254, International Preliminary Report on Patentability mailed Oct. 14, 21", 8 pages.
"International Application Serial No. PCT/US2020/026254, International Search Report mailed Sep. 1, 2020", 5 pgs.
"International Application Serial No. PCT/US2020/026254, Invitation to Pay Additional Fees mailed Jun. 12, 2020", 2 pgs.
"International Application Serial No. PCT/US2020/026254, Written Opinion mailed Sep. 1, 2020", 6 pgs.
Compton, et al., "Chemically Active Reduced Graphene Oxide with Tunable ClO Ratios", ACS Nano, vol. 5, No. 6, (Apr. 7, 2011), 4380-4391.
Li, et al., "ZnO@graphene composite with enhanced performance for the removal of dye from water", Journal of Materials Chemistry, vol. 21, (Nov. 8, 2010), 3346-3349.
Nath, et al., "Light tuning DC and AC electrical properties of ZnO—rGO based hybrid nanocomposite film", Journal of Applied Physics, vol. 123, article No. 095115, (Mar. 7, 2018).
Yang, et al., "Facile Fabrication of Functionalized Graphene Sheets (FGS)/ZnO Nanocomposites with Photocatalytic Property", ACS Applied Materials and Interfaces, vol. 3,, (Jun. 17, 2011), 2770-2785.
Zhang, et al., "A facile one-pot route for the controllable growth of small sized and well-dispersed ZnO particles on GO-derived graphene", vol. 22, (Apr. 18, 2012), 11778-11784.

* cited by examiner

*Primary Examiner* — Patricia L. Hailey
(74) *Attorney, Agent, or Firm* — Schwegman Lundberg & Woessner, P.A.

(57) ABSTRACT

Various embodiments provide a zinc oxide graphene composite. A zinc oxide graphene composite includes zinc oxide crystallites and graphene. A method of forming the composite includes combining graphene and zinc oxalate to form a mixture and heating the mixture to produce the zinc oxide graphene composite.

20 Claims, 11 Drawing Sheets

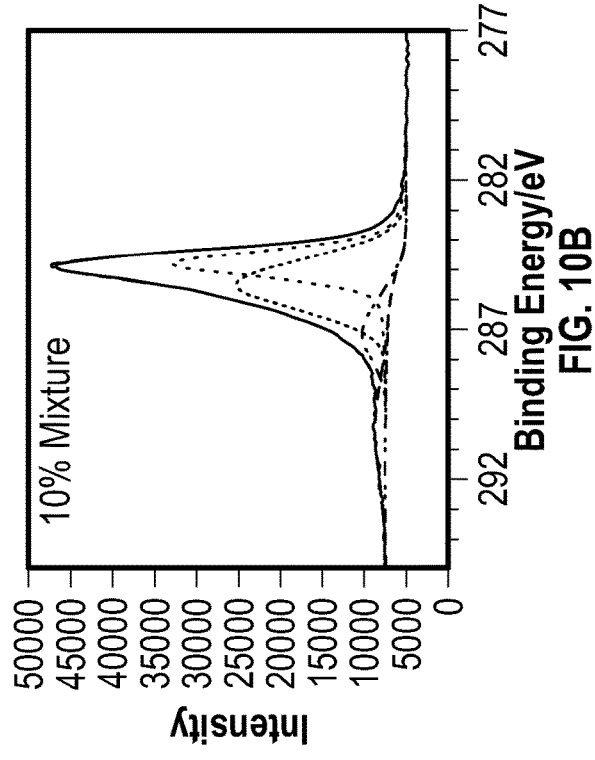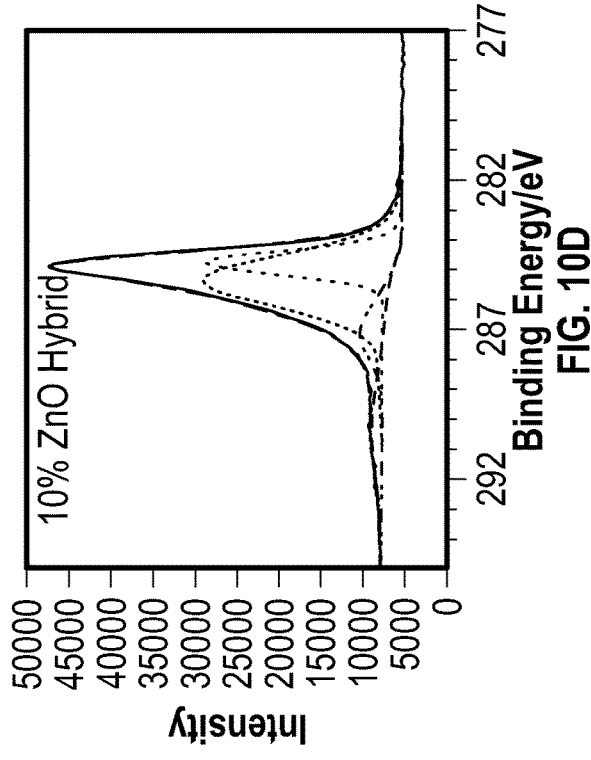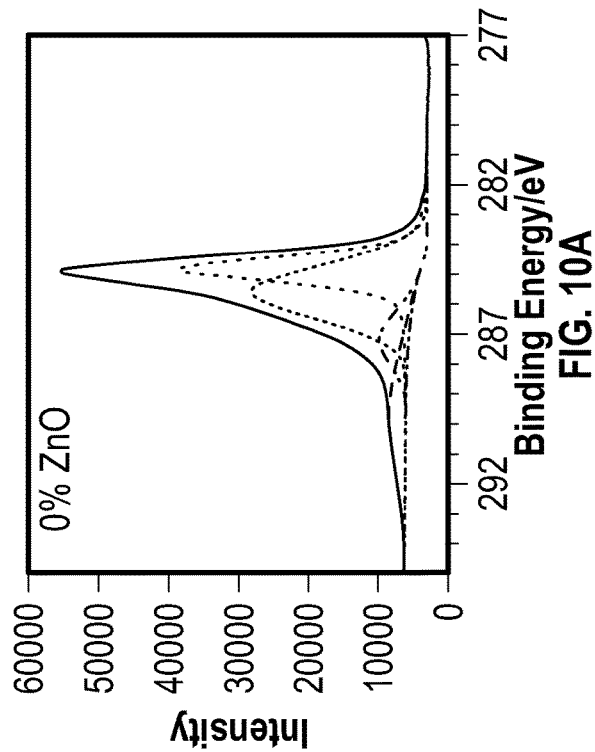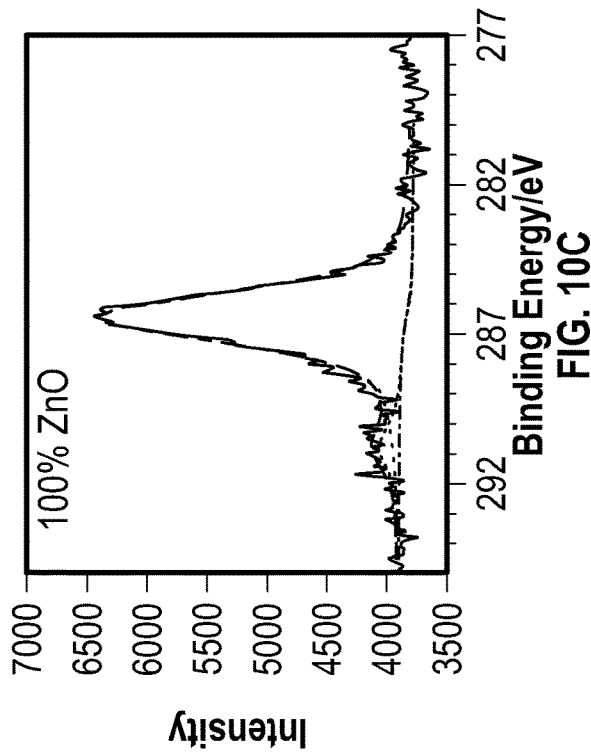

ZINC OXIDE GRAPHENE COMPOSITE

CLAIM OF PRIORITY

This patent application is a U.S. National Stage Filing under 35 U.S.C. 371 from International Application No. PCT/US2020/026254, filed Apr. 1, 2020, which claims the benefit of priority to U.S. Provisional Application Ser. No. 62/828,001, filed Apr. 2, 2019, each of which are incorporated by reference herein in their entirety.

STATEMENT OF GOVERNMENT SUPPORT

This invention was made with Government support under contract number 144-4-367653 (CFDA 43.008) awarded by the National Aeronautics and Space Administration and under contract number 144-4-367610 (CFDA 47.049) awarded by the National Science Foundation.

BACKGROUND

Hybrid or composite materials of zinc oxide (ZnO) and graphene or reduced graphene oxide are currently of interest in the materials science community because they are inexpensive, non-toxic, and boast a spectrum of useful applications. For example, they have seen use as photocatalysts, sensors, capacitors, and as transparent conductive thin-films, among other applications.

Zinc oxide and graphene composite materials have been synthesized in a number of ways. For example, some fabrication methods involve either solvothermal or sol-gel techniques, electrodeposition of the material, or solution-based synthesis involving pH manipulation of a $Zn^{2+}$ ion precursor.

Some methods synthesize ZnO/graphene composites through thermal decomposition of zinc acetate dihydrate $(Zn(CH_3COO_2k)_2 \cdot 2H_2O)$ in slurry or in a solid-state solution with a graphene precursor. However, thermal decomposition of $Zn(CH_3COO)_2 \cdot 2H_2O$ results in the formation of excess amorphous carbon, which is an impurity in the finished product.

SUMMARY OF THE DISCLOSURE

In various embodiments a zinc oxide graphene composite includes zinc oxide crystallites and graphene.

In various embodiments, a zinc oxide graphene composite includes zinc oxide crystallites that are about 0.1 mol. % to about 12 mol. % of the composite, wherein the zinc oxide crystallites have a crystallite size of about 15 to about 37 crystallite size, and graphene chemically bonded to the zinc oxide through bridging oxygen atoms, wherein carbon is about 75 mol. % to about 98 mol. % of the composite.

In various embodiments, a method of making a zinc oxide graphene composite includes combining graphene and zinc oxalate $(ZnC_2O_4)$ to form a mixture and heating the mixture to produce the zinc oxide graphene composite.

In various embodiments, a method of making a zinc oxide graphene composite includes combining graphene and zinc oxalate to form a mixture, wherein the graphene and the zinc oxalate in the mixture are solids, suspending the mixture in a solvent, agitating the mixture such that at least some aggregates of the graphene break apart, removing the solvent, dehydrating the mixture by heating the mixture, further mixing the graphene and the zinc oxalate, and decomposing the zinc oxalate in the mixture to produce zinc oxide, comprising heating the mixture to produce a composite zinc oxide and graphene material wherein the graphene is bonded to the zinc oxide through bridging oxygen atoms.

In various embodiments, an article comprising a zinc oxide graphene composite includes a photocatalyst, sensor, capacitor, transparent conductive thin-film, or a combination thereof.

In some embodiments, the thermal decomposition of $ZnC_2O_4$ in a homogeneous solid-state solution with graphene is an inexpensive, safe, and industrially viable method for synthesizing a ZnO/graphene hybrid material.

In some embodiments, the graphitic environment inhibits the ZnO nanocrystal growth pattern, resulting in small ZnO crystallite sizes. In some embodiments, the graphitic environment allows formation of bridging oxygen atoms which serve to hold the two phases of the hybrid together via chemical bonds. This endows the resulting hybrid material chemical properties that are different from those observed from a solid-state mixture of graphene and ZnO nanoparticles of the same stoichiometry.

BRIEF DESCRIPTION OF THE FIGURES

The drawings illustrate generally, by way of example, but not by way of limitation, various embodiments discussed in the present document.

FIGS. 10A-10D show high-resolution XPS scans of the C 1s regions of Example 5 ("0% ZnO"), Example 6 ("100% ZnO"), Example 2 ("10% ZnO"), and Example 7 ("10% mixture"), in accordance with various embodiments.

Figure 1A:
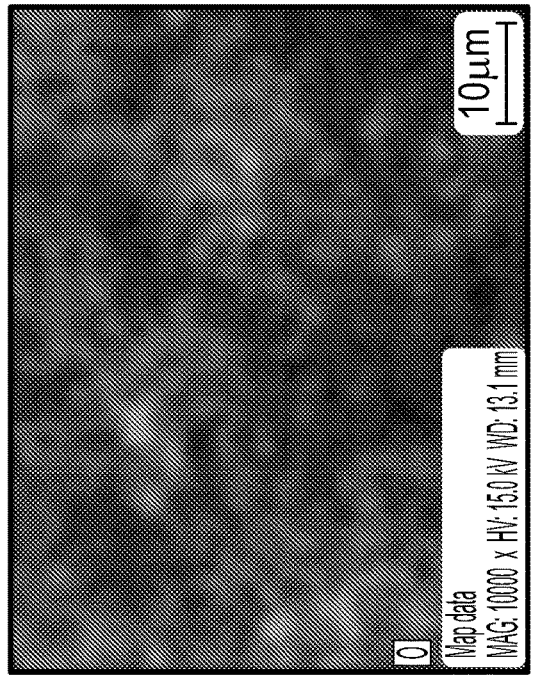
FIGS. 1A-1D are representative scanning electron microscope (SEM) images of Example 2 ("10% ZnO"), showing spatially mapped signals for carbon, zinc, and oxygen atoms in the region, in accordance with various embodiments.
Figure 1B:
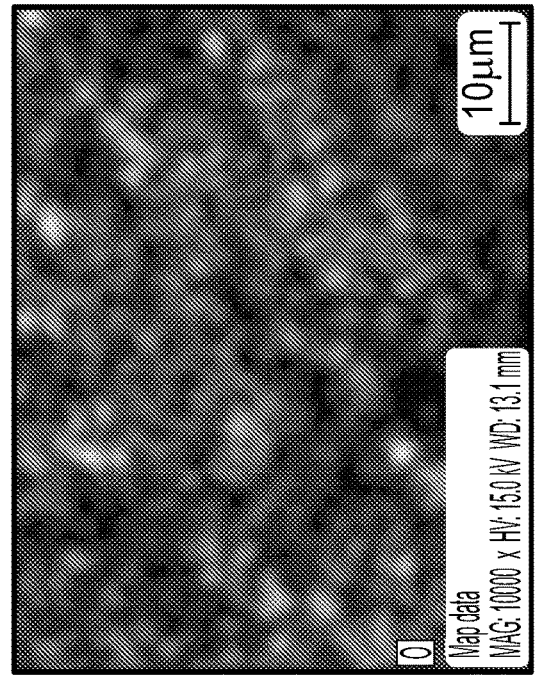
Figure 1C:
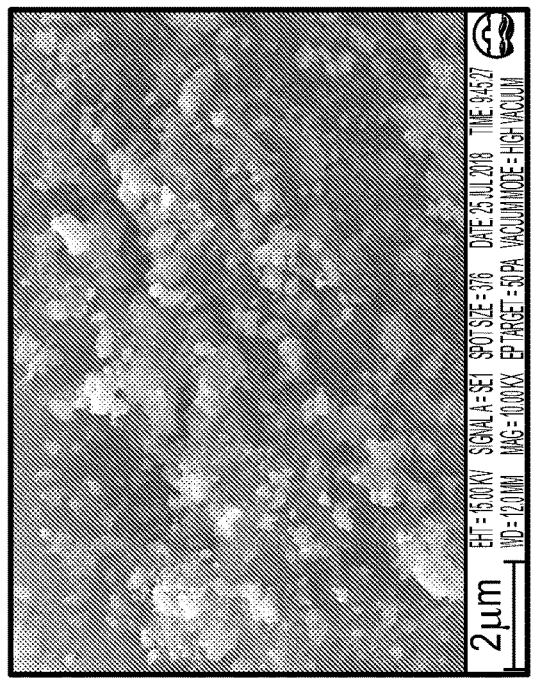
Figure 1D:
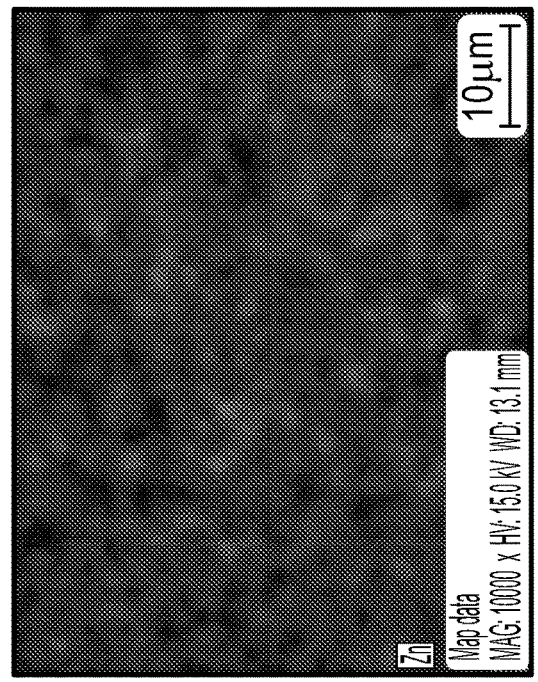
Figure 2A:
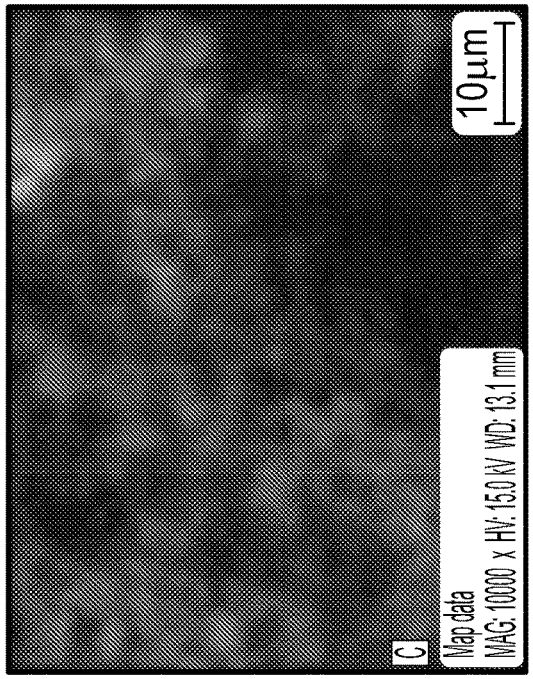
FIGS. 2A-2D are representative SEM images of Example 7 ("10% mixture"), showing spatially mapped signals for carbon, zinc, and oxygen atoms in the region, in accordance with various embodiments.
Figure 2B:
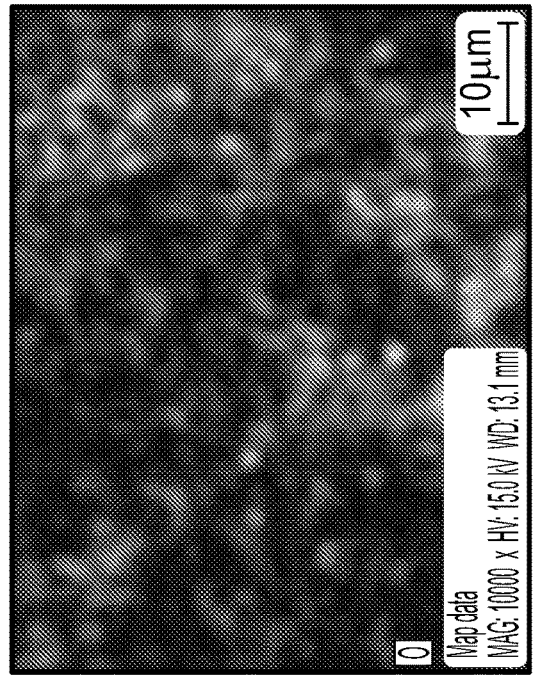
Figure 2C:
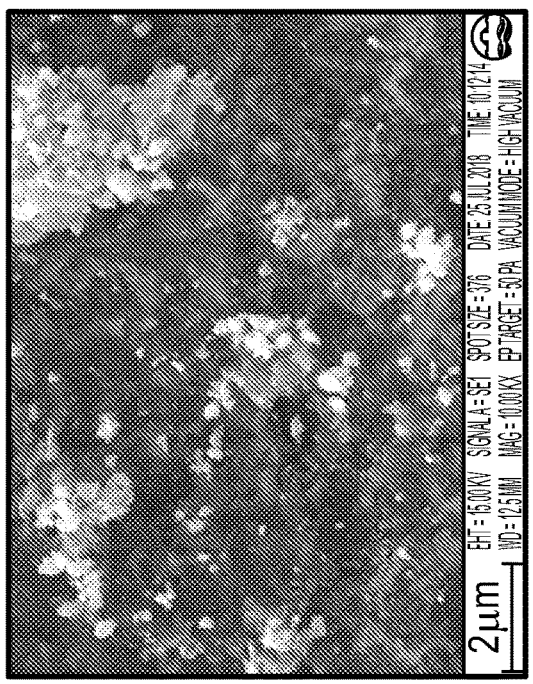
Figure 2D:
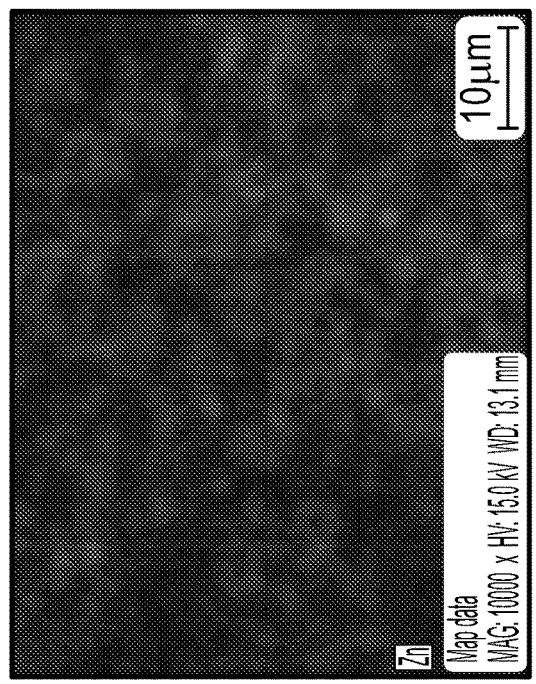
Figure 3A:
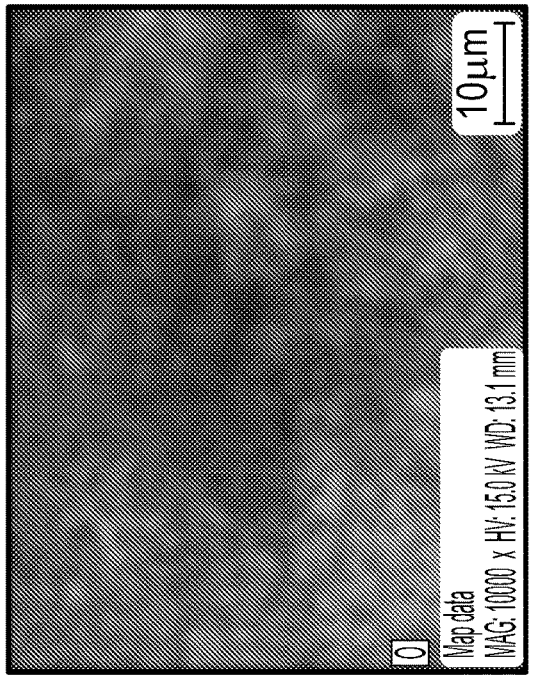
FIGS. 3A-3D are representative SEM images of Example 6 ("100% ZnO"), showing spatially mapped signals for carbon, zinc, and oxygen atoms in the region, in accordance with various embodiments.
Figure 3B:
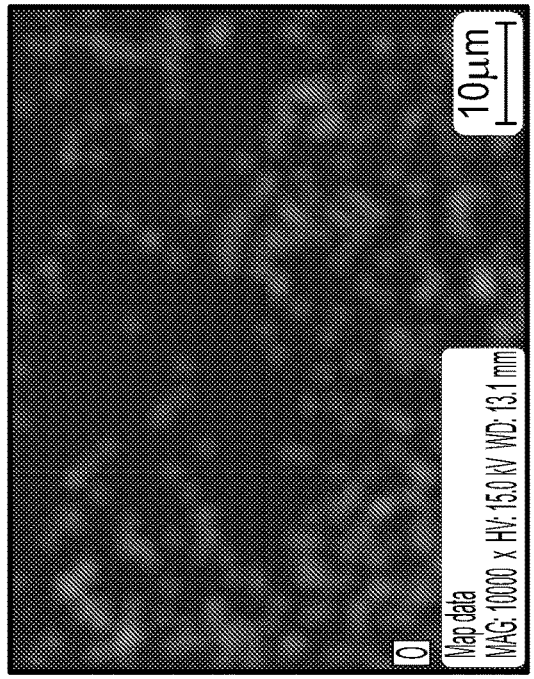
Figure 3C:
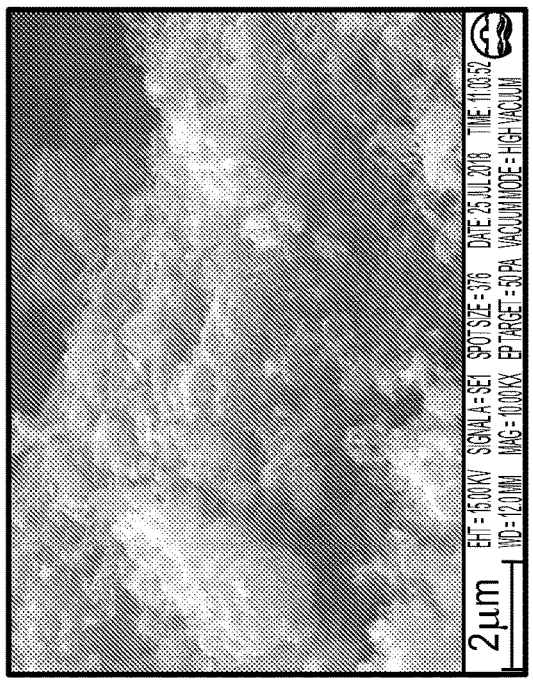
Figure 3D:
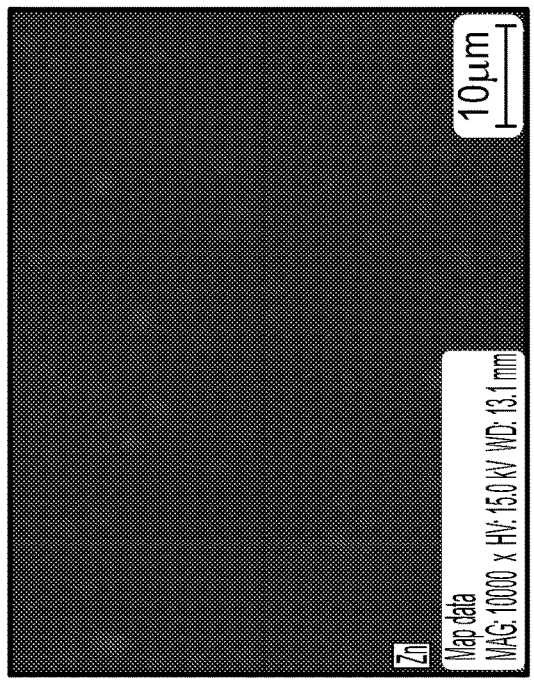
Figure 4B:
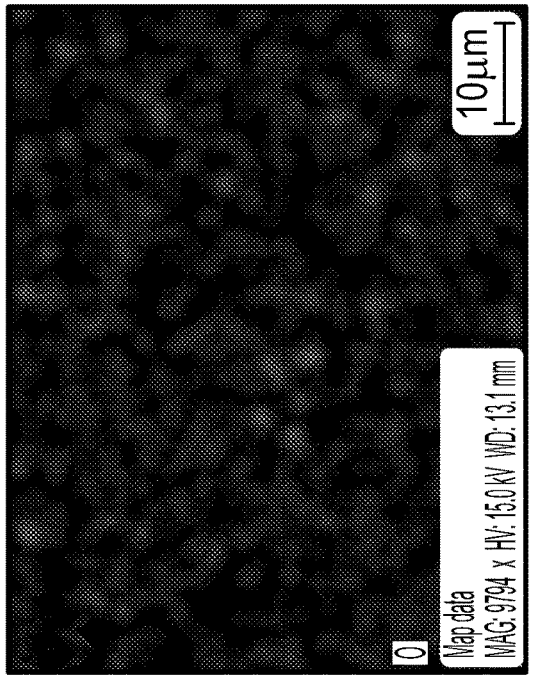
FIGS. 4A-4D are representative SEM images of Example 5 ("0% ZnO"), showing spatially mapped signals for carbon, zinc, and oxygen atoms in the region, in accordance with various embodiments.
Figure 4D:
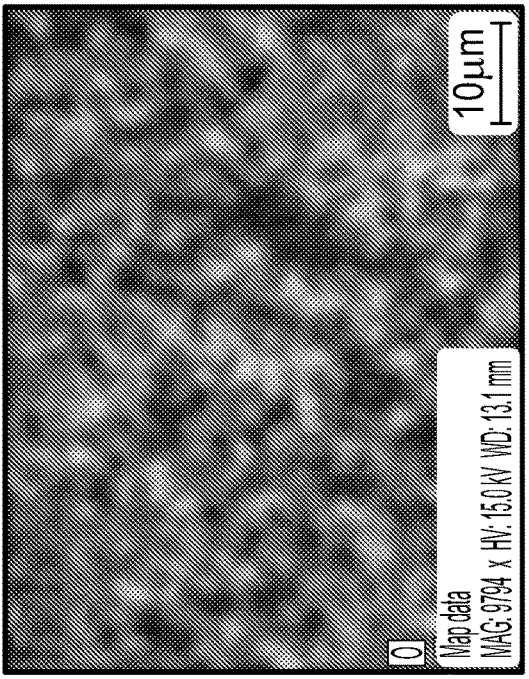
Figure 4A:
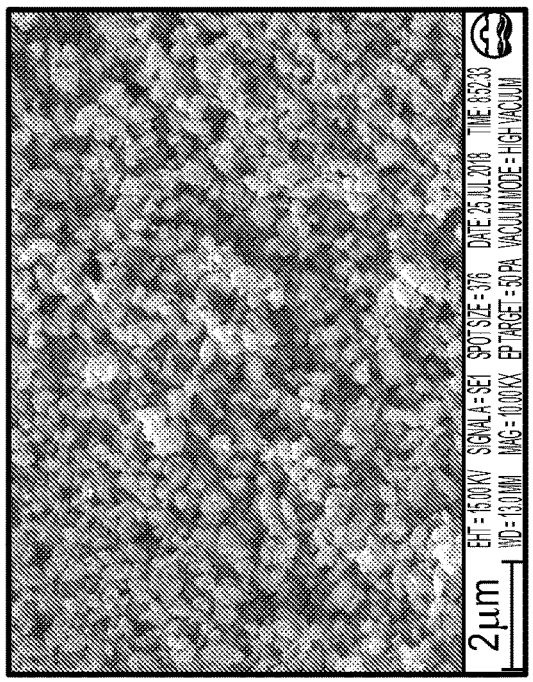
Figure 4C:
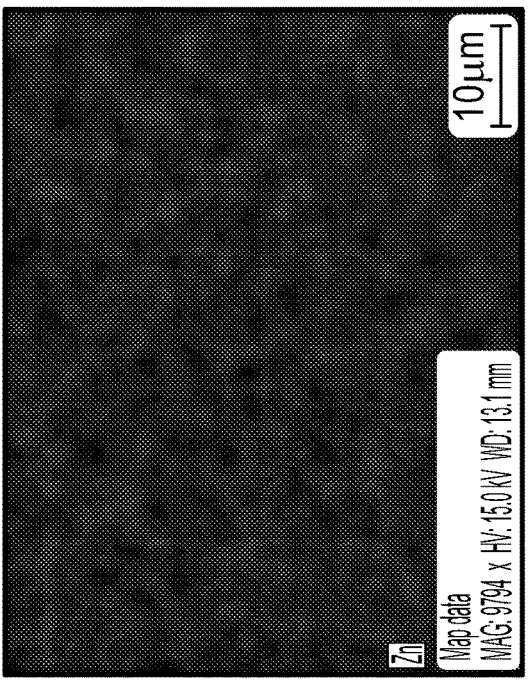

("100% ZnO"), Example 2 ("10% ZnO"), and Example 7 ("10% mixture"), in accordance with various embodiments.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "infrared" as used herein refers to electromagnetic radiation with a wavelength between about 0.7 micrometers and about 300 micrometers.

The term "solvent" as used herein refers to a liquid that can dissolve a solid, liquid, or gas. Non-limiting examples of solvents are silicones, organic compounds, water, alcohols, ionic liquids, and supercritical fluids.

The term "room temperature" as used herein refers to a temperature of about 15° C. to 28° C.

The term "crystallite" as used herein refers to an individual crystal or region of regular crystalline structure in the substance of a material having smaller or microscopic form.

Overview

It is desirable to begin with a zinc compound that will thermally decompose into only ZnO and other gaseous byproducts. A solid-state thermal method is preferred due to the minimal equipment requirements, and straight-forward industrial scalability, as such a method is simple, safe, and cost-effective.

The decomposition of zinc oxalate dihydrate ($ZnC_2O_4 \cdot 2H_2O$) has been demonstrated to occur in two stages: the dehydration of the complex, followed by decomposition to ZnO, carbon monoxide (CO), and carbon dioxide ($CO_2$), as shown in Equations 1 and 2. Product formation is temperature dependent in these reactions. The rate of decomposition is determined by nucleation and growth of the ZnO phase. Under an aerobic environment, the overall process becomes exothermic as there is a secondary oxidation of the CO product to $CO_2$ catalyzed by the newly formed ZnO sites, as shown in Equation 3. Thus, when heated in air, ZnO, $H_2O$, and $CO_2$ are the only products of the decomposition reaction.

$$ZnC_2O_4 \cdot 2H_2O \xrightarrow{T<90° C.} ZnC_2O_4 + 2H_2O \quad (1)$$

$$ZnC_2O_4 \xrightarrow{T>300° C.} ZnO + CO + CO_2 \quad (2)$$

$$CO + \frac{1}{2}O_2 \rightarrow CO_2 \quad (3)$$

The relatively simple decomposition pathway of $ZnC_2O_4$ is useful to synthesize a ZnO/graphene hybrid structure. This synthetic method uses inexpensive materials and is simple to perform. The slow nucleation of ZnO crystals within the graphitic matrix allows for electronic interaction between the two phases, which leads to chemical properties that are different from a mere homogeneous solid-state solution.

Zinc Oxide Graphene Composite

In various embodiments, the present invention provides zinc oxide graphene composite. The composite can contain zinc oxide crystallites and graphene. The graphene can be bonded to the zinc oxide crystallites through bridging oxygen atoms. The composite can include a zinc oxide domain and a graphene domain. The zinc oxide domain can include zinc oxide crystallites. The graphene domain can include graphene. The zinc oxide domain and the graphene domain can be homogenously distributed in the zinc oxide graphene composite.

The zinc oxide crystallites can be zinc (II) oxide. In some embodiments, the composite can contain between about 15 and 37 nm zinc oxide crystallite size. In other embodiments, the composite can contain between about 15 and 18 nm zinc oxide crystallite size.

The composite can contain varying amounts of zinc, carbon, and oxygen. In various embodiment, the composite can have a composition containing from about 0.05 mol. % zinc to about 55 mol. % zinc, in some embodiments the composite can have a composition containing from about 0.1 mol. % zinc to about 12 mol. % zinc.

In various embodiments, the composite can have a composition containing from about 6 mol. % carbon to about 99 mol. % carbon, in some embodiment the composite can have a composition containing from about 75 mol. % carbon to about 98 mol. % carbon.

In various embodiment, the composite can have a composition containing from about 1 mol. % oxygen to about 45 mol. % oxygen, in some embodiment the composite can have a composition containing from about 1.5 mol. % oxygen to about 15 mol. % oxygen.

Methodology

In various embodiments, the present invention provides a method of making a zinc oxide graphene composite. The method can include combining graphene to form a mixture and heating the mixture to produce the zinc oxide graphene composite. The combining can create a homogenous mixture of zinc oxalate and graphene. Both the zinc oxalate and graphene can be solids when combined. The graphene can be graphene nanoplatelet aggregates. In some embodiments, combining the graphene and zinc oxalate can be done by physical means such as a mortar and pestle.

In various embodiments, the method can include suspending the mixture in a reasonably nonvolatile ultrapure solvent, such as Millipore water, alcohols, or acetone. If Millipore water is used, Polyethylene Glycol (PEG) can optionally be added to raise the boiling point of the solvent. The method can include agitation of the mixture in solvent to break up any graphene aggregates, such as by ultrasonicating. Alternatively, a prepared aqueous suspension of graphene could be used, or a large area graphene film. This allows for prevention of graphite mesoparticles in the mixture. In some embodiments, the solvent can then be removed through heating, for example, to 100° C. for Millipore water, or other appropriate temperature based on the solvent.

In various embodiments, the heating can follow the suspension and can dehydrate the zinc oxalate, which can be in the form of a dihydrate. Dehydrating the mixture can be done by heating the mixture about to 200° C.

In various embodiments, after dehydrating the mixture, zinc oxalate and graphene can separate into distinct layers. Thus, the graphene and zinc oxalate can be re-mixed, for example, by mortar and pestle, or other solid mixture methods appropriate in the art.

In various embodiments, subsequent heating can decompose the zinc oxalate. To produce zinc oxide and carbon dioxide. Decomposing the mixture can be done by heating the mixture to about 400° C. to about 600° C. Decomposition by heating can occur over a long period of time to allow for complete zinc oxalate decomposition and mixture annealing.

In various embodiments, zinc oxalate dihydrate can be synthesized prior to making the zinc oxide graphene composite. Synthesizing the zinc oxalate dihydrate can be done, for example, by combining a zinc salt and an oxalate salt. In some embodiments, the oxalate salt can be ammonium oxalate, and the zinc salt can be zinc nitrate hexahydrate, or alternatively zinc salts with nitrate, chloride, sulfate or other materials as appropriate. In various embodiments, the zinc salt and the oxalate salt can be combined in solution. The zinc oxalate dihydrate can then be precipitated and vacuum filtered.

EXAMPLES

Various embodiments of the present disclosure can be better understood by reference to the following Examples which are offered by way of illustration. The present disclosure is not limited to the Examples given herein.

Instrumentation used in examples. MP-AES was conducted using an Agilent 4100 MP-AES. Scanning Electron Microscopy (SEM) images were recorded using a Zeiss EVO-HD instrument employing a Bruker Energy Dispersive Spectroscopy (EDS) accessory for elemental analysis. Powder X-ray diffraction (XRD) was conducted using Siemens D500 X-ray Defractometer. X-ray photoelectron spectra of the products were obtained with a Phi 5100 XPS system using an Al anode. Attenuated total reflectance infrared (ATR-IR) spectroscopy employed a Thermo Scientific iS50 ATR.

Example 1

Synthesis and Characterization of Zinc Oxalate Precursor

Zinc oxalate ($ZnC_2O_4$) was synthesized by precipitating it from near-saturated solutions of ammonium oxalate (($NH_4)_2C_2O_4$, Fisher, ACS) and zinc nitrate hexahydrate ($Zn(NO_3)_2 \cdot 6H_2O$, Alfa Aesar, 99%). To begin, 4.5 g of ($NH_4)_2C_2O_2$ was dissolved in 100 mL of Millipore water, and 8.0 g of $Zn(NO_3)_2 \cdot 6H_2O$ was separately dissolved in 5 mL of Millipore water. The zinc solution was slowly dripped into the oxalate solution using a Pasteur pipette at room temperature. The precipitate was allowed to settle to the bottom of the beaker before decanting most of the solvent, followed by vacuum filtration. The hydrated product, $ZnC_2O_4 \cdot 2H_2O$, was pre-dried in a vacuum oven at 80° C. to remove residual solvent. Then, the white powder was heated in a furnace at 200° C. to dehydrate the crystals, resulting in pure $ZnC_2O_4$. Heating to 200° C. causes dehydration of the complex without decomposition of the oxalate ion, according to thermogravimetric analysis data for $ZnC_2O_4$.

The dehydrated $ZnC_2O_4$ was characterized using MP-AES to determine the mass percent of Zn. The precursor contained 5.46 mmol Zn for every gram of powder. The ideal amount would be 6.52 mmol, indicating a fair amount of residual water or ($NH_4)_2C_2O_4$ in the product. A key advantage of the decomposition method, however, is that residual water will evaporate and residual ($NH_4)_2C_2O_4$ will decompose into ammonia ($NH_3$) and carbon dioxide ($CO_2$) gasses leaving the desired product. As a result, the precursor was used without further purification, and 5.46 mmol per gram of powder was used as the Zn concentration for stoichiometric calculations.

Examples 2-4

Synthesis of Zinc Oxide-Graphene Hybrid Material

Zinc Oxide-Graphene Hybrid material was synthesized using the $ZnC_2O_4$ from Example 1. Graphene flakes (Graphene nanoplatelet aggregates, sub-micron particles, S.A. 500 $m^2$/g, Alfa Aesar) were used as the graphene precursor. Stoichiometric amounts of solid $ZnC_2O_4$ from Example 1 and graphene flake precursors were measured using a balance, and then mixed using a mortar and pestle. Samples were mixed to create C:Zn mole ratios of 10:1, 100:1, and 1000:1, and are referred to as Example 2 ("10% ZnO"), Example 3 ("1% ZnO"), and Example 4 ("0.1% ZnO") respectively. Each of the mixtures was suspended in 15 mL of Millipore water and ultrasonicated (Fisher 550 Sonic Disembrator) at 15% power for 30 minutes. This broke apart graphene aggregates, which are mesoparticles of graphite. The suspensions were then heated to 100° C. to remove the liquid water, and then to 200° C. to completely dehydrate the powder, and to remove water that may have been added during earlier ultrasonication. Slowly dehydrating in this manner allowed the graphene and $ZnC_2O_4$ to separate into discrete layers, so each sample was then removed from the furnace and thoroughly re-mixed using mortar and pestle. The samples were then heated to 450° C. for 6 hours to allow for complete precursor decomposition and product annealing.

Examples 5-7

Synthesis of Controls

Both Example 5, "0% ZnO" and Example 6, "100% ZnO" controls were synthesized using the method of Example 2 as described above. However, in the synthesis of Example 5 ("0% ZnO"), no $ZnC_2O_4$ precursor was added to the mixture. In the synthesis of Example 6 ("100% ZnO") no graphene flakes precursor was added. Examples 5 and 6 (the controls) were still heated in the furnace in two stages, and ground with mortar and pestle in between.

Additionally, Example 7, a "10% mixture" control, was created by mixing 0.060 g of the Example 5 ("0% ZnO") control with 0.039 g of the Example 6 ("100% ZnO") control using mortar and pestle, but not any additional heating. This was to reflect the Example 2 ("10% ZnO") product stoichiometry.

Example 8

Analysis of Results

The mole percentages of carbon (C), oxygen (O), and zinc (Zn) in each of the Examples 2-7 were identified using EDS, and the results are shown in Table 1 below. EDS provides a relatively rough idea of elemental stoichiometry, though it is evident that the product Zn concentrations were slightly higher than anticipated, particularly in Example 3 ("1% ZnO"). There is typically carbon impurity on the order of 1-2% in all EDS spectra due to atmospheric carbon (dust) incorporating into the sample. There may have been a small amount of un-decomposed oxalate still present in Example 6 ("100% ZnO"), resulting in an atomic percentage of 6.5% carbon. Elemental mapping was used to get an idea of the distribution of C, O, and Zn in each of Examples 2-7. FIGS. 1A-1D show an example of individual elemental signals mapped onto an SEM image of Example 2 ("10% ZnO"). Maps and SEM images of Examples 5, 6, and 7 are shown in FIGS. 2A-2D, 3A-3D, and 4A-4D. Elemental mapping showed that the ZnO domains and graphitic domains are homogeneously distributed through the hybrid material.

TABLE 1

Mole percentage of C, O, and Zn in Examples 2-7.

| Example | C/% | O/% | Zn/% |
|---|---|---|---|
| Example 2 "10% ZnO" | 77.0 | 12.2 | 10.7 |
| Example 3 "1% ZnO" | 93.5 | 3.7 | 2.7 |
| Example 4 "0.1% ZnO" | 97.8 | 1.9 | 0.3 |
| Example 5 "0% ZnO" | 98.3 | 1.7 | 0.0 |
| Example 6 "100% ZnO" | 6.5 | 41.5 | 52.0 |
| Example 7 "10% mixture" | 81.2 | 10.9 | 8.0 |

Figure 5B:
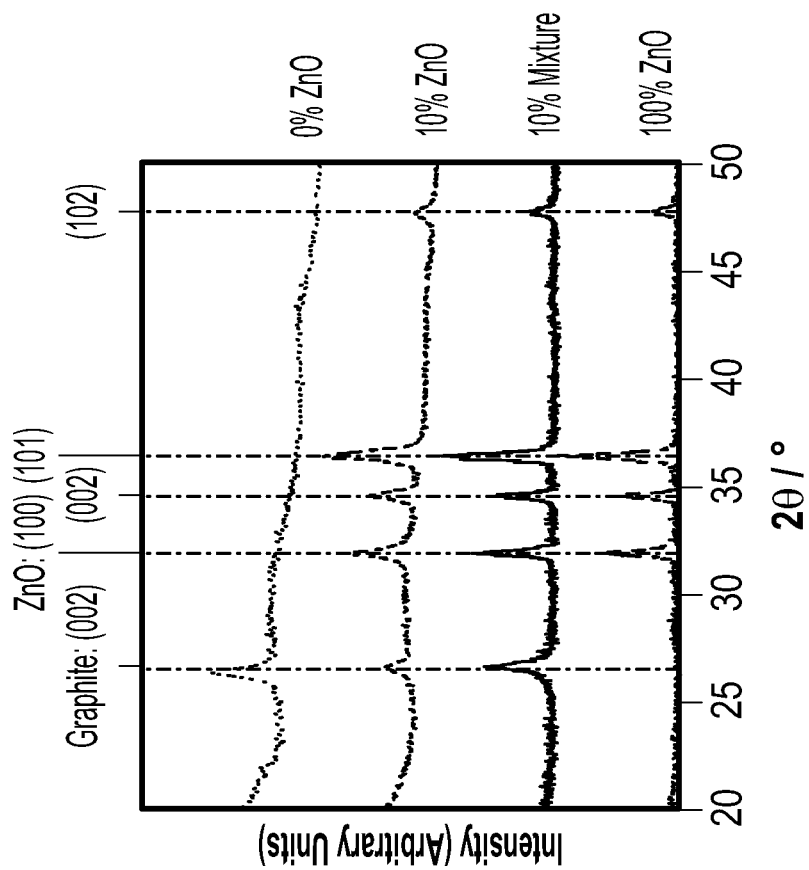
FIGS. 5A-5B are powder x-ray diffraction (XRD) spectra of each of Examples 2-7, in accordance with various embodiments.
Figure 5A:
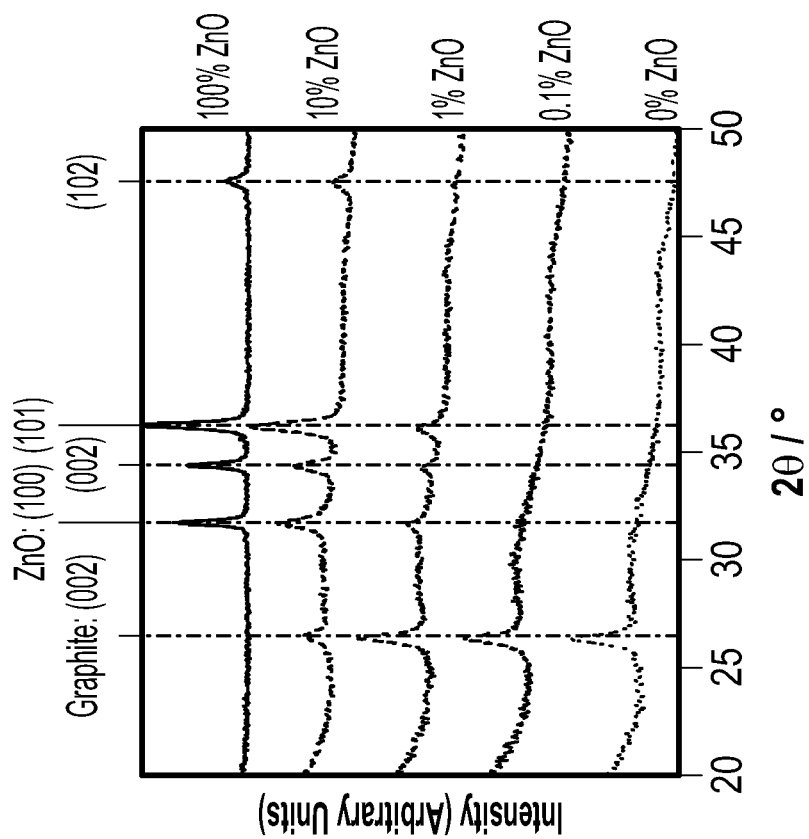

Powder XRD patterns of each of Examples 2-7 are shown in FIGS. 5A-5B. From a first-order comparison of FIG. 5A, the spectrum of Example 6 ("100% ZnO") matched JCPDS data for ZnO, while the spectrum of Example 5 ("0% ZnO") reflected reported patterns for graphene aggregates (mesoparticles of graphite). The single, sharp peak at 26.5° in the Example 5 ("0% ZnO") spectrum is indicative of the graphite (002) crystallite orientation referred to as a reflection, and the broad background peaks indicate an overall structure that is amorphous. FIG. 5A shows the intensity of the graphite (002) peak decreases and the intensities of the ZnO peaks at 31.8°, 34.4°, 36.2°, and 47.5° all increase when comparing Example 4 ("0.1% ZnO") to Example 3 ("1% ZnO") to Example 2 ("10% ZnO"), following the relative concentrations of graphene and ZnO respectively.

FIG. 5B allowed for comparison of Example 2 ("10% ZnO") and Example 7 ("10% mixture"). A first-order comparison showed that the normalized intensity of the graphene (002) peak at 26.5° for Example 7 ("10% mixture") was larger than that of Example 2 ("10% ZnO"), despite the stoichiometry of the Examples being approximately the same. The full width half max (FWHM) in Example 2 ("10% ZnO") spectrum of each of the four ZnO peaks between 30° and 50° was wider than in either Example 7 ("10% mixture") or Example 6 ("100% ZnO").

The FWHM of a peak in powder XRD can be read to indicate the crystallite size. Thus, the Scherrer equation was used to approximate the mean size of each ZnO crystalline domain as a function of the wavelength of the instrument (0.154 nm in this case). The Scherrer equation is shown below in Equation 4, where L is the average linear dimension of a crystallite in a given direction, K is a dimensionless "shape factor" which is typically close to unity, $\lambda$ is the wavelength of the instrument, $\beta$ is the FWHM of the peak in radians, and $\theta$ is the Bragg angle in radians.

$$L = \frac{K\lambda}{\beta \cos\theta} \quad (4)$$

Figure 6:
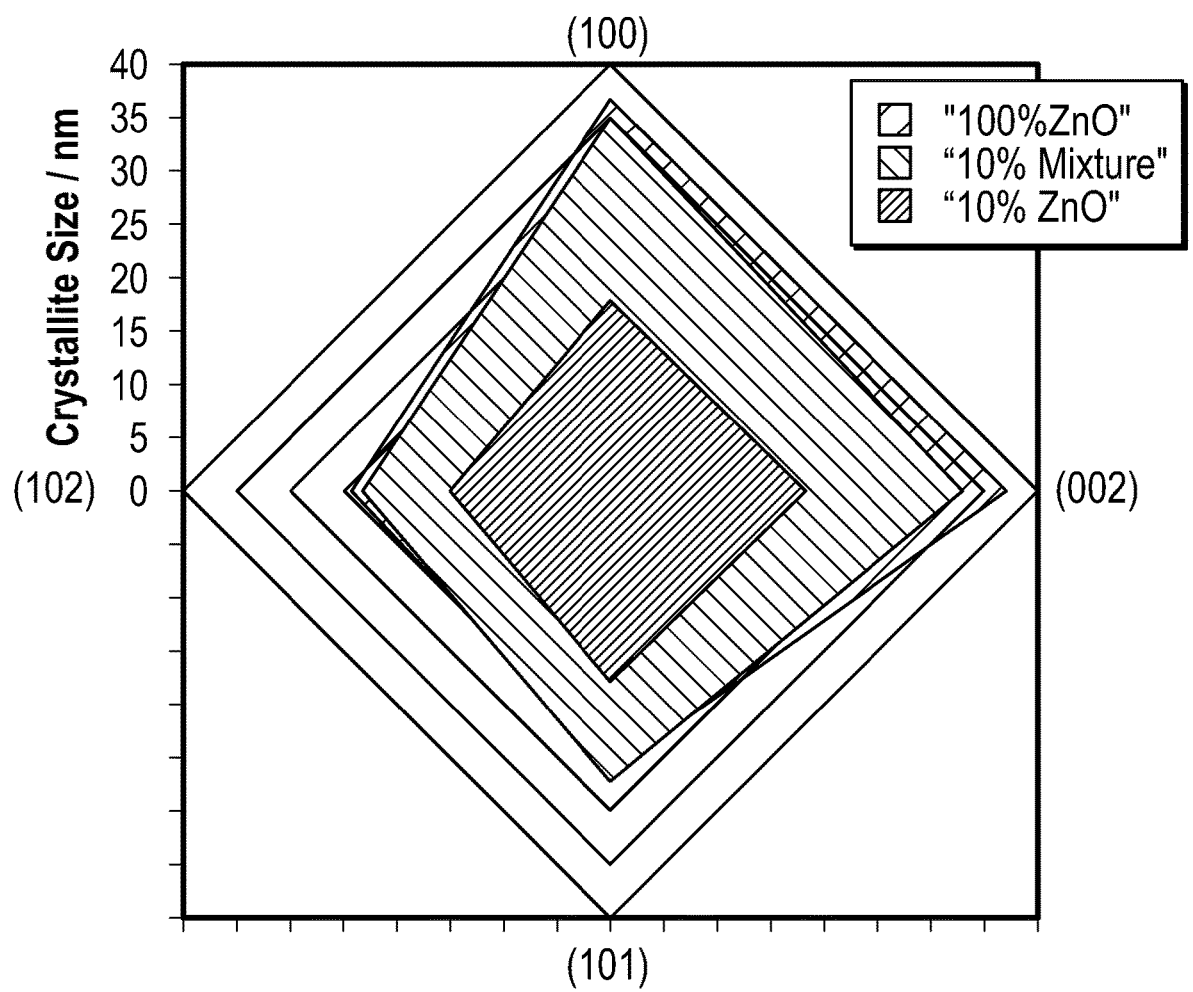
FIG. 6 shows a graphical representation of the comparison of the ZnO crystallite sizes of Example 6 ("100% ZnO"), Example 2 ("10% ZnO"), and Example 7 ("10% mixture") as approximated by the Scherrer equation, in accordance with various embodiments.

Assuming that K is unity, the ZnO crystallite sizes of Example 2 ("10% ZnO"), Example 7 ("10% mixture"), and Example 6 ("100% ZnO") are shown numerically in Table 2 below, and graphically in FIG. 6. K was likely a value closer to 0.9 or even smaller, but this would only serve to linearly decrease all calculated values and not affect the comparison.

TABLE 2

Comparison of the ZnO crystallite sizes of Examples 2, 6, and 7.

| | Approximate Crystallite Size (nm) | | | |
|---|---|---|---|---|
| Sample | (100) | (002) | (101) | (102) |
| Example 2 "10%ZnO" | 18 | 18 | 18 | 15 |
| Example 6 "100% ZnO" | 37 | 37 | 27 | 24 |
| Example 7 "10% Mixture" | 35 | 33 | 27 | 23 |

The FWHM for the Example 7 ("10% mixture") and Example 2 ("100% ZnO") spectra were very close, as Example 7 contained ZnO from Example 6 ("100% ZnO"). On average, the ZnO crystallite size were smaller in all directions in Example 2 ("10% ZnO") than it is in either of Examples 6 or 7 (the controls)—nearly by a factor of 2. Additionally, the ZnO crystal growth seemed to favor the (100) direction in Examples 6 and 7 (the controls), while growth was much more uniform in all directions in Example 2 ("10% ZnO"). This indicates that the ZnO particles in the synthesized sample were different from those in the homogeneous mixture. It is likely that the high-carbon environment during the decomposition and annealing phase of the synthesis affected ZnO crystal growth. It is possible that the $ZnC_2O_4$ decomposition pathway was altered by the solid-state solution, thus discouraging crystallization of ZnO. Synthesis of the hybrid material by this method encouraged interaction between the ZnO and graphitic due to the proximity of mixing ZnO and graphene into a solid-state solution.

Figure 7:
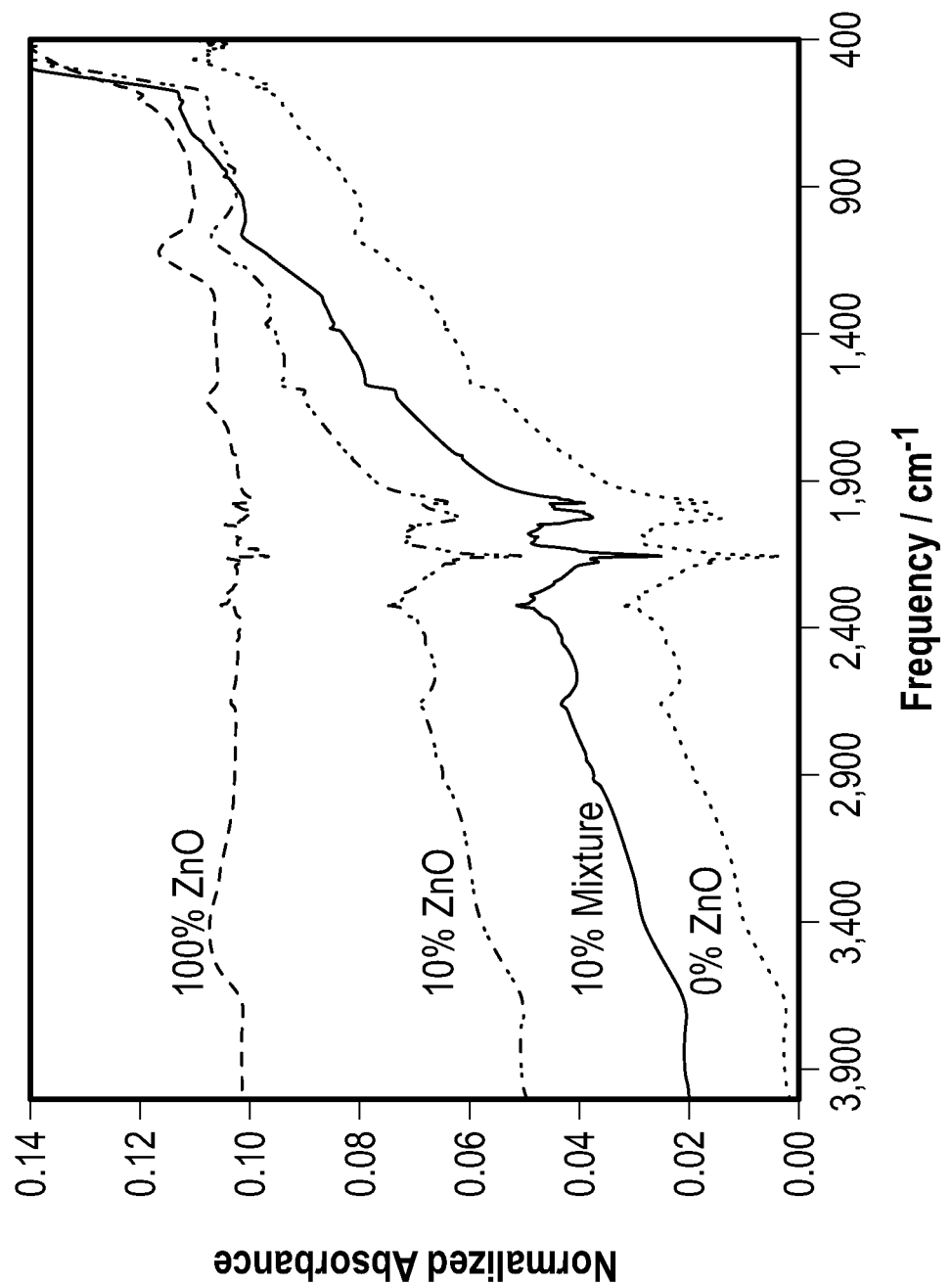
FIG. 7 shows the attenuated total reflection infrared (ATR-IR) spectra of Example 5 ("0% ZnO"), Example 7 ("10% mixture"), Example 6 ("100% ZnO"), and Example 2 ("10% ZnO"), in accordance with various embodiments.
Figure 8A:
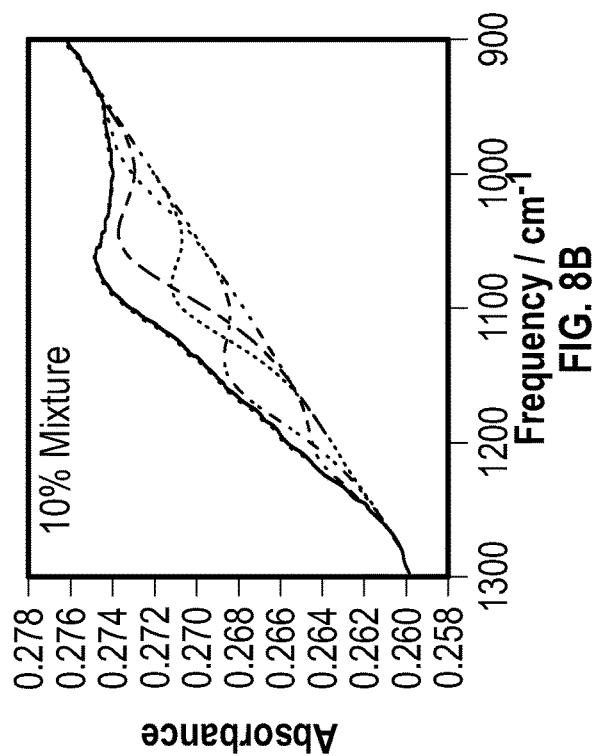
FIGS. 8A-8D show ATR-IR spectra of Example 5 ("0% ZnO"), Example 6 ("100% ZnO"), Example 2 ("10% ZnO"), and Example 7 ("10% mixture"), in accordance with various embodiments.
Figure 8B:
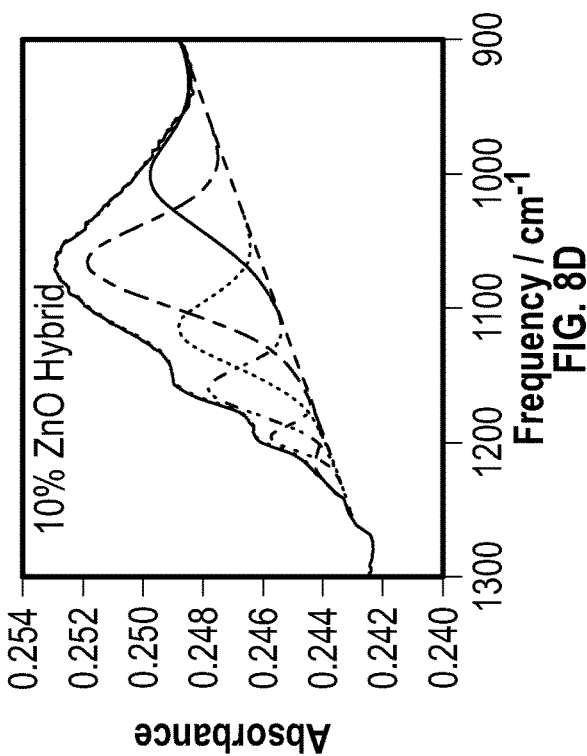
Figure 8C:
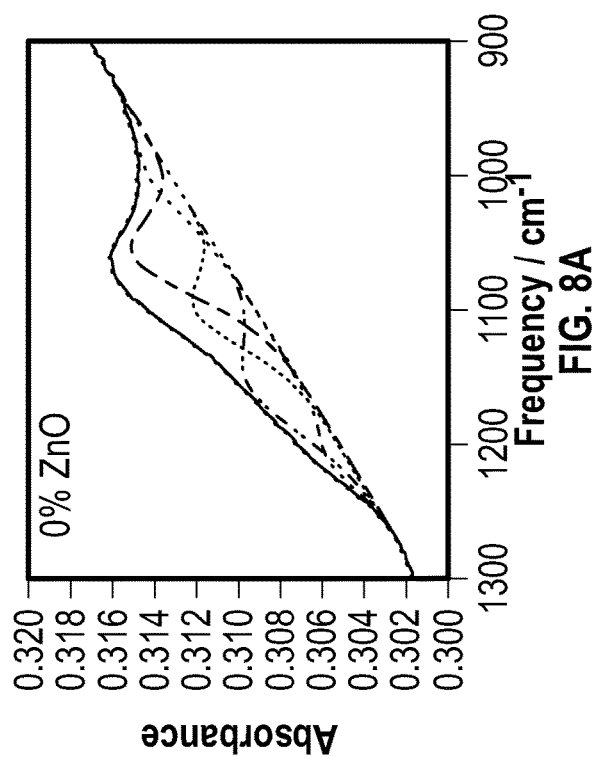
Figure 8D:
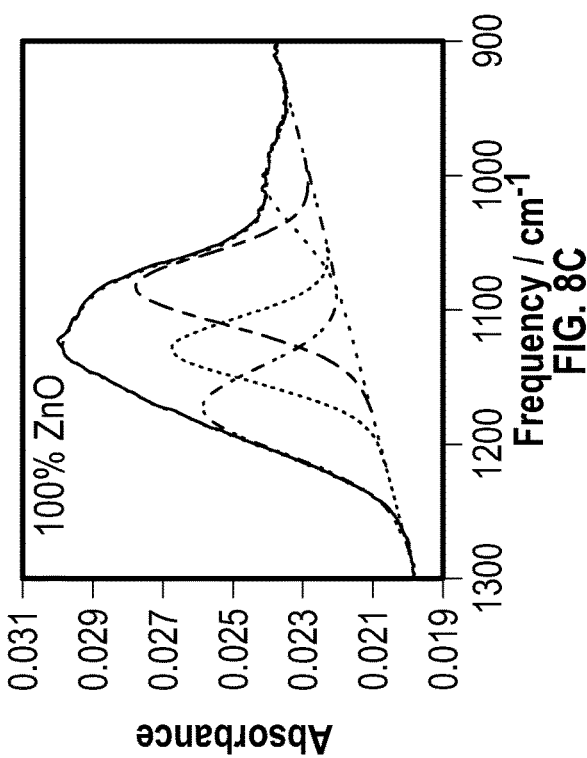
Figure 9A:
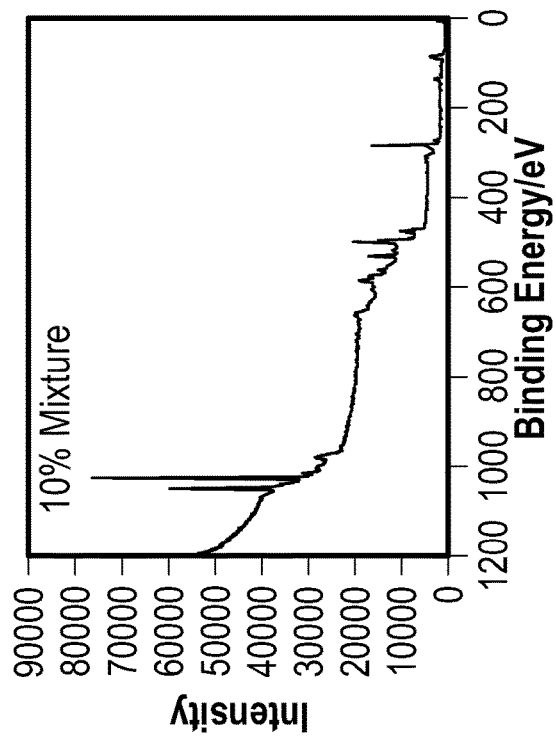
FIGS. 9A-9D show x-ray photoelectron spectroscopy (XPS) survey scans of Example 5 ("0% ZnO"), Example 6 ("100% ZnO"), Example 2 ("10% ZnO"), and Example 7 ("10% mixture"), in accordance with various embodiments.
Figure 9B:
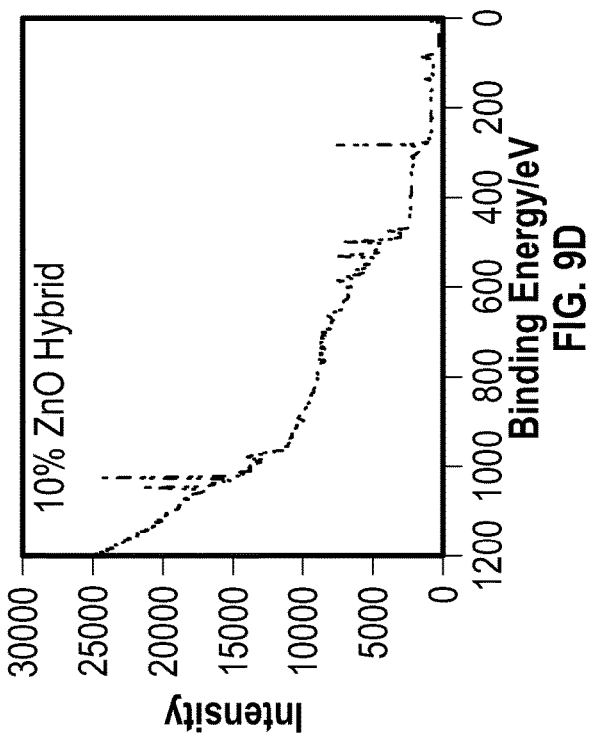
Figure 9C:
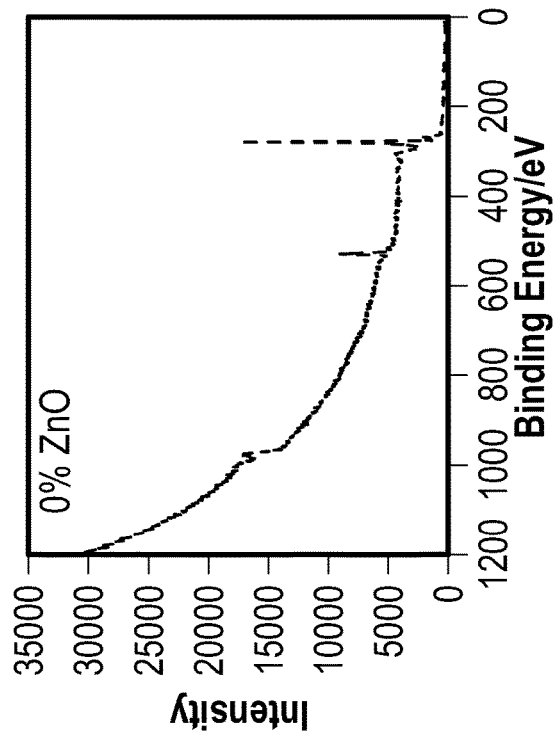
Figure 9D:
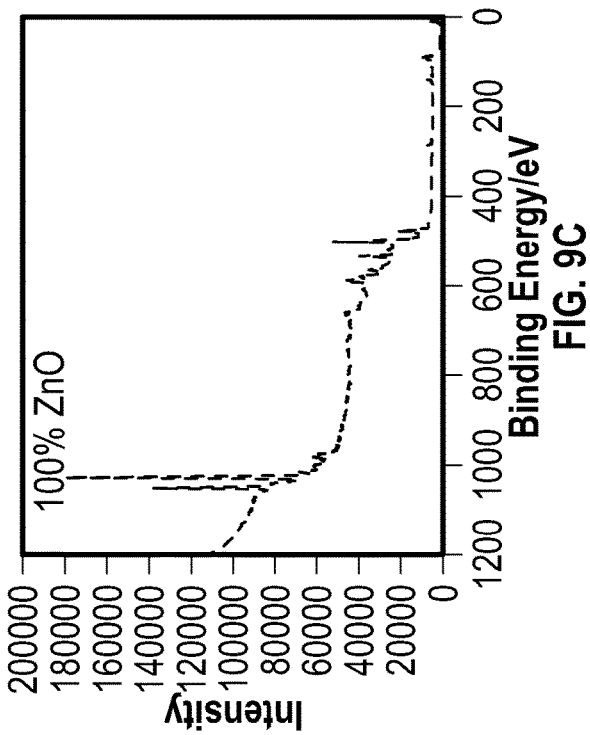

To probe the chemical bonds of the hybrid material Examples, ATR-IR was utilized. Since graphene absorbs so strongly in essentially all regions of the electromagnetic spectrum, including the IR, each sample was diluted by a factor of 100 using potassium bromide (KBr, Kodak, technical grade), as KBr has no significant absorption features in the region of interest. The full spectra for each of the samples are shown in FIG. 7. An excerpt of the region of interest can be seen in FIGS. 8A-8D. Absorption bands in this region are typically associated with carbon-oxygen bonds, such as the inevitable terminal oxygen impurities in the graphitic phase, or possibly oxygen atoms bridging carbon atoms and zinc atoms between the two hybrid phases. Ignoring vertical offsets, Example 7 ("10% mixture") shown in FIG. 8B was very close to Example 5 ("0% ZnO") shown in FIG. 8A. However, Example 2 ("10% ZnO") in FIG. 8D had distinct extra features at between 1200 and 1100 $cm^{-1}$.

TABLE 3

Gaussian fit peak positions for the ATR-IR data shown in FIGS. 8A-8D.

| Sample | Example 2 10% ZnO | Example 5 0% ZnO | Example 6 100% ZnO | Example 7 10% Mixture |
|---|---|---|---|---|
| Peak Positions/ $cm^{-1}$ | 1010 | 1003 | 1009 | 994 |
| | 1070 | 1061 | — | 1057 |
| | — | 1102 | 1084 | 1096 |
| | 1119 | — | 1129 | — |
| | 1163 | 1158 | — | 1155 |
| | 1198 | — | 1174 | — |
| | 1221 | 1210 | — | 1212 |

All of the spectra in FIGS. 8A-8D were fit using Gaussian curves, the results of which are shown in Table 3 for direct comparison. With the exception of the peak at 1212 $cm^{-1}$, the peaks in Example 2 ("10% ZnO mixture") spectrum were redshifted by about 5 $cm^{-1}$, allowing the peaks to be reasonably assigned to related, if not identical vibrational phenomena. The Example 2 ("10% ZnO") spectrum contained features that are not present in the Example 5 ("0% ZnO") or the Example 7 ("10% mixture") spectra. A comparison of the fits of the four spectra indicates that Example 2 (the "10% ZnO" sample) shows vibrational modes that are not related to either the pure graphitic phase, or the pure ZnO phase, or the appropriate mixture of the two. These are new vibrational modes related to chemical bond formation between the ZnO and graphitic phases of the hybrid material; likely through a Zn—O—C bridging oxygen mode.

XPS allowed for probing of different environments of C and O atoms within the Examples by effectively measuring their 1s orbital energies. XPS survey scans for the four Examples studied are shown in FIGS. 9A-9D. High resolution scans of the carbon 1s and oxygen 1s regions are shown in FIGS. 10A-10D and 11A-11D, respectively. The peak parameters of the de-convoluted spectra are shown in Table 4 below.

TABLE 4

De-convoluted peak parameters of the C 1s spectra of FIGS. 10A-10D.

| Example | Position/eV | Area | FWHM | % Lorentzian |
|---|---|---|---|---|
| Example 2 | 284.8 | 25687 | 0.96 | 15 |
| 10% ZnO | 285.4 | 52401 | 2.08 | 14 |
| | 287.2 | 5142 | 1.91 | 0 |
| | 290.2 | 4406 | 3.52 | 0 |
| Example 5 | 284.8 | 44481 | 1.00 | 40 |
| 0% ZnO | 285.6 | 53154 | 2.14 | 0 |
| | 287.2 | 8736 | 1.93 | 0 |
| | 289.7 | 10878 | 3.52 | 0 |
| Example 6 | 286.4 | 6565 | 1.97 | 47 |
| 100% ZnO | 290.8 | 388 | 1.71 | 50 |
| Example 7 | 284.8 | 35869 | 1.04 | 39 |
| 10% Mixture | 285.5 | 39994 | 2.00 | 1 |
| | 287.1 | 6896 | 2.17 | 0 |
| | 290.3 | 4499 | 3.47 | 0 |

The C 1s region scans are a close reflection of the ATR-IR data in FIGS. 8A-8D: The Example 5 ("0% ZnO") and Example 7 ("10% mixture") spectra are similar to each other, while there is a subtle difference present in the Example 2 ("10% ZnO") spectrum. The Example 6 ("100% ZnO") spectrum, as established by EDS in Table 1, has a much lower carbon content than the other Examples, and this is reflected by the nearly ten-fold lower signal in FIG. 10C. This signal is likely due to residual $ZnC_2O_4$, or some other carbon-containing impurity, as well as any adventitious carbon signal typical to XPS spectra. Since both of those sources involve $sp^2$ C═O carbon sites, their signals are convoluted into one peak at 286.4 eV. In the spectra of the remaining Examples, the peak at about 284.8 eV is attributed to graphitic $sp^2$ carbon. The peaks around 285.4 and 287.1 eV are attributed to C—O and C═O respectively, and the very broad peak around 290 eV is the result of the $sp^2$ carbon $\pi \rightarrow \pi^*$ "shake-up" satellite.

Figure 11A:
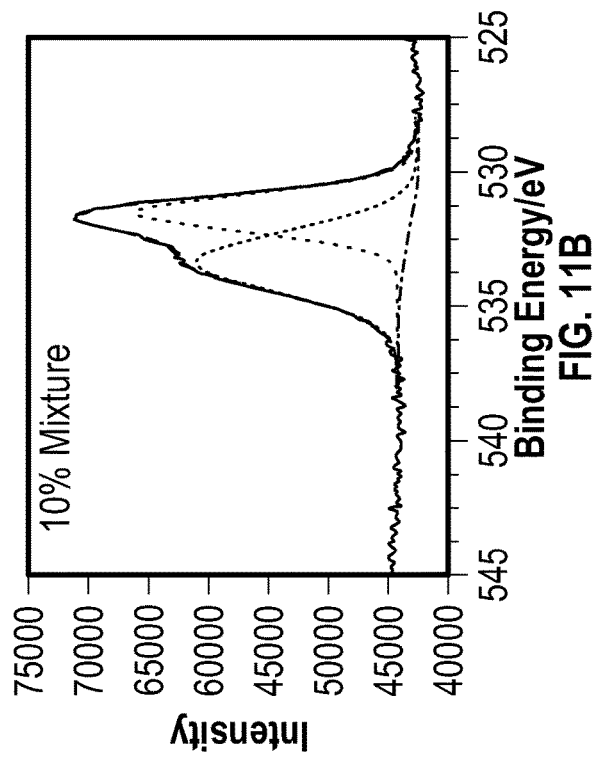
FIGS. 11A-11D illustrate high-resolution XPS scans of the O 1s is regions of Example 5 ("0% ZnO"), Example 6
Figure 11B:
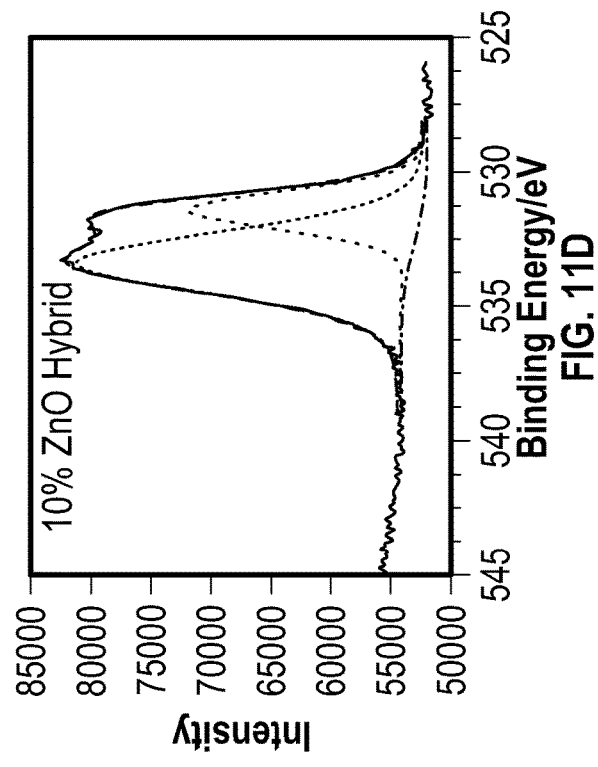
Figure 11C:
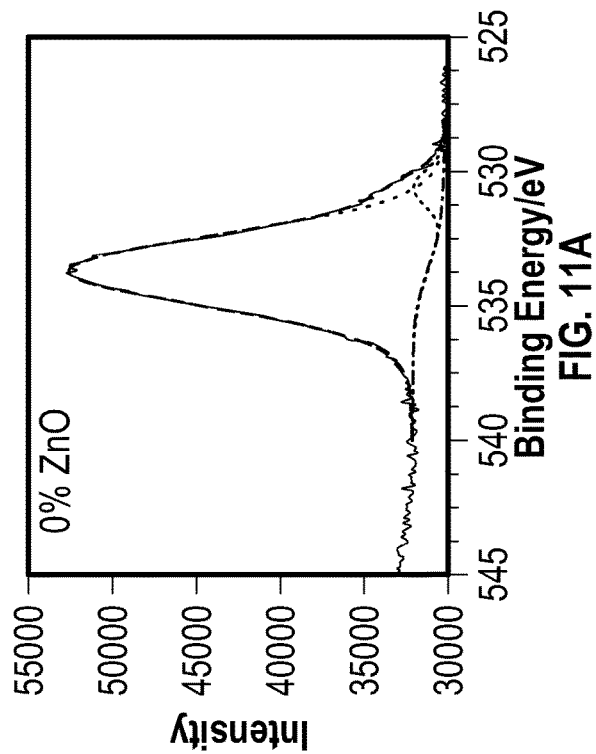

The O 1s region scan of Example 5 ("0% ZnO"), shown in FIG. 11A, reflects a fairly typical surface-oxidized graphene spectrum. In the other Examples 2, 6, and 7, the first group of peaks are centered at about 531.5 eV with a FWHM of about 1.6, and the second group of peaks are centered at about 533 eV with a FWHM of about 2.6. These similarities in width and binding energy suggest that all three Examples 2, 6, and 7, contain oxygen atoms primarily in two common environments. The peaks near 531.5 eV are attributed to O atoms within the ZnO lattice. The other peaks near 533 eV are attributed to terminal O atoms. The broad range of possible terminal O atom environments contributes to the much broader FWHM of the peaks near 533 eV.

Figure 11D:
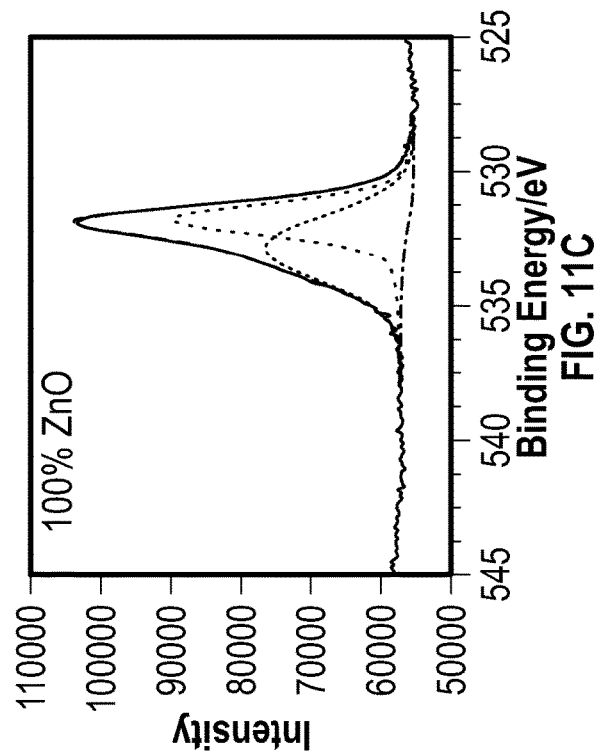

FIG. 11D indicates that the ratio of terminal O atoms to ZnO lattice atoms is much larger in Example 2 ("10% ZnO") than it is in Example 7 ("10% mixture"). This is due in part to the smaller ZnO crystallite size in Example 2 as indicated by XRD in FIG. 6. As nanoparticles decrease in size, the number of internal atoms decreases much more quickly than the number of surface atoms, thus increasing the terminal to lattice O ratio. However, it is evident from FIG. 10D that the number of C—O single bonds is significantly larger in Example 2 ("10% ZnO") compared to Example 7 ("10% mixture"), as the peak at 285.4 eV is approximately 1.3-fold larger in area. This fact, and the appearance of completely new C—O vibrational modes in FIG. 8D, suggests the existence of bridging O atoms (C—O—Zn) in Example 2 that are not present in Example 7. While these bridging atoms are not strictly "terminal", as they are between the graphitic and ZnO phases, one would still expect their 1s electrons to have similar binding energy—it is still an $sp^3$ hybridized O bonded to atoms significantly more electropositive than itself, (C, H, and/or Zn).

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Additional Embodiments

The following exemplary embodiments are provided, the numbering of which is not to be construed as designating levels of importance:

Embodiment 1 provides a zinc oxide graphene composite includes zinc oxide crystallites and graphene.

Embodiment 2 provides the composite of Embodiment 1, wherein the graphene is bonded to the zinc oxide through bridging oxygen atoms.

Embodiment 3 provides the composite of any of Embodiments 1-2, wherein the zinc oxide graphene composite includes a zinc oxide domain comprising the zinc oxide crystallites and a graphene domain including the graphene, wherein the zinc oxide domain and the graphene domain are homogeneously distributed in the zinc oxide graphene composite, and wherein the zinc oxide graphene composite is substantially free of other domains.

Embodiment 4 provides the composite of any of Embodiments 1-3, wherein the zinc oxide crystallites are zinc(II) oxide.

Embodiment 5 provides the composite of any of Embodiments 1-4, wherein the composite is about 0.05 mol. % to about 55 mol. % zinc.

Embodiment 6 provides the composite of any of Embodiments 1-5, wherein the composite is about 0.1 mol. % to about 12 mol. % zinc.

Embodiment 7 provides the composite of any of Embodiments 1-6, wherein the composite is about 6 mol. % to 99 mol. % carbon.

Embodiment 8 provides the composite of any of Embodiments 1-7, wherein the composite is about 75 mol. % to 98 mol. % carbon.

Embodiment 9 provides the composite of any of Embodiments 1-8, wherein the composite is about 1 mol. % to about 45 mol. % oxygen.

Embodiment 10 provides the composite of any of Embodiments 1-9, wherein the composite is about 1.5 mol. % to about 15 mol. % oxygen.

Embodiment 11 provides the composite of any of Embodiments 1-10, wherein the zinc oxide has a crystallite size of about 15 to about 37 crystallite size.

Embodiment 12 provides the composite of any of Embodiments 1-11, wherein the zinc oxide has a crystallite size of about 15 to about 18 crystallite size.

Embodiment 13 provides a zinc oxide graphene composite includes zinc oxide crystallites that are about 0.1 mol. % to about 12 mol. % of the composite, wherein the zinc oxide crystallites have a crystallite size of about 15 to about 37 crystallite size, and graphene chemically bonded to the zinc oxide through bridging oxygen atoms, wherein carbon is about 75 mol. % to about 98 mol. % of the composite.

Embodiment 14 provides a method of making the zinc oxide graphene composite of any of Embodiments 1-13 that includes combining graphene and zinc oxalate to form a mixture and heating the mixture to produce the zinc oxide graphene composite.

Embodiment 15 provides the method of Embodiment 14.

Embodiment 16 provides the method of any of Embodiments 14-15, wherein the graphene comprises graphene nanoplatelet aggregates.

Embodiment 17 provides the method of any of Embodiments 14-16, wherein the graphene and the zinc oxalate in the mixture are solids.

Embodiment 18 provides the method of any of Embodiments 14-17, wherein dehydrating the mixture is done at about 100° C. to about 200° C.

Embodiment 19 provides the method of any of Embodiments 14-18, wherein decomposing the mixture is done at about 400° C. to about 600° C.

Embodiment 20 provides the method of any of Embodiments 14-19, further comprising suspending the mixture in a solvent.

Embodiment 21 provides the method of any of Embodiments 14-20, further comprising agitating the mixture such that at least some aggregates of the graphene break apart.

Embodiment 22 provides the method of any of Embodiments 14-21, further comprising removing the solvent.

Embodiment 23 provides the method of any of Embodiments 14-22, further comprising re-mixing any separated zinc oxalate prior to decomposing the mixture.

Embodiment 24 provides the method of any of Embodiments 14-23, further comprising forming the zinc oxalate.

Embodiment 25 provides the method of any of Embodiments 14-24, wherein forming the zinc oxalate further comprises combining an oxalate salt and a zinc salt to form zinc oxalate dihydrate.

Embodiment 26 provides the method of any of Embodiments 14-25, wherein the oxalate salt and the zinc salt are combined in solution.

Embodiment 27 provides the method of any of Embodiments 14-26, wherein the oxalate salt is ammonium oxalate.

Embodiment 28 provides the method of any of Embodiments 14-27, wherein the zinc salt is zinc nitrate hexahydrate.

Embodiment 29 provides the method of any of Embodiments 14-28, further comprising precipitating and vacuum filtering the zinc oxalate dihydrate.

Embodiment 30 provides a method of making a zinc oxide graphene composite includes combining graphene and zinc oxalate to form a mixture, wherein the graphene and the zinc oxalate in the mixture are solids, suspending the mixture in a solvent, agitating the mixture such that at least some aggregates of the graphene break apart, removing the solvent, dehydrating the mixture by heating the mixture, further mixing the graphene and the zinc oxalate, and decomposing the zinc oxalate in the mixture to produce zinc oxide, comprising heating the mixture to produce a composite zinc oxide and graphene material wherein the graphene is bonded to the zinc oxide through bridging oxygen atoms.

Embodiment 31 provides a composite made by any of the methods of Embodiments 14-31.

Embodiment 32 provides, an article comprising a zinc oxide graphene composite includes a photocatalyst, sensor, capacitor, transparent conductive thin-film, conductive paint, conductive polymer or a combination thereof.

What is claimed is:

1. A zinc oxide graphene composite comprising:
   zinc oxide crystallites that are about 0.1 mol. % to about 12 mol. % of the composite; and
   graphene chemically bonded to the zinc oxide through bridging oxygen atoms, wherein carbon is about 75 mol. % to about 98 mol. % of the composite.

2. A zinc oxide graphene composite comprising:
   zinc oxide crystallites; and
   graphene;
   wherein the composite is about 0.05 mol % to about 55 mol. % zinc.

3. The zinc oxide graphene composite of claim 2, wherein the graphene is bonded to the zinc oxide through bridging oxygen atoms.

4. The zinc oxide graphene composite of claim 2, wherein the zinc oxide graphene composite comprises:
   a zinc oxide domain comprising the zinc oxide crystallites; and
   a graphene domain comprising the graphene, wherein the zinc oxide domain and the graphene domain are homogeneously distributed in the zinc oxide graphene composite, and wherein the zinc oxide graphene composite is substantially free of other domains.

5. The zinc oxide graphene composite of claim 2, wherein the composite is about 1 mol. % to about 45 mol. % oxygen.

6. The zinc oxide graphene composite of claim 2, wherein the zinc oxide has a crystallite size of about 15 to about 37.

7. An article comprising the composite of claim 2, wherein the article comprises a photocatalyst, sensor, capacitor, transparent conductive thin-film, conductive paint, conductive polymer, or a combination thereof.

8. The zinc oxide graphene composite of claim 2, wherein the composite is about 6 mol. % to 99 mol. % carbon.

9. The zinc oxide graphene composite of claim 1, wherein the composite is about 6 mol. % to 99 mol. % carbon.

10. A method of making zinc oxide graphene composite, comprising:
    combining graphene and zinc oxalate to form a mixture; and
    heating the mixture to produce the zinc oxide graphene composite.

11. The method of claim 10, wherein the graphene comprises graphene nanoplatelet aggregates.

12. The method of claim 10, wherein heating the mixture comprises:
    dehydrating the mixture; and
    decomposing the mixture.

13. The method of claim 12, wherein dehydrating the mixture is done at about 100° C. to about 200° C.

14. The method of claim 10, further comprising suspending the mixture in a solvent.

15. The method of claim 14, further comprising agitating the mixture such that at least some aggregates of the graphene break apart.

16. The method of claim 10, further comprising re-mixing any separated zinc oxalate prior to decomposing the mixture.

17. The method of claim 10, further comprising forming the zinc oxalate.

18. The method of claim 17, wherein forming the zinc oxalate further comprises combining an oxalate salt and a zinc salt to form zinc oxalate dihydrate.

19. The method of claim 18, wherein the oxalate salt and the zinc salt are combined in solution.

20. A method of making a zinc oxide composite, the method comprising:
    combining graphene and zinc oxalate to form a mixture, wherein the graphene and the zinc oxalate in the mixture are solids;
    suspending the mixture in a solvent;
    agitating the mixture such that at least some aggregates of the graphene break apart;
    removing the solvent;
    dehydrating the mixture by heating the mixture;
    further mixing the graphene and the zinc oxalate; and
    decomposing the zinc oxalate in the mixture to produce zinc oxide, comprising heating the mixture to produce the zinc oxide composite comprising zinc oxide crystallites and graphene, wherein the graphene is bonded to the zinc oxide through bridging oxygen atoms.

* * * * *